United States Patent
Toyama et al.

(10) Patent No.: US 10,081,620 B2
(45) Date of Patent: Sep. 25, 2018

(54) RADIOACTIVE FLUORINE LABELING PRECURSOR COMPOUND AND METHOD FOR MANUFACTURING RADIOACTIVE FLUORINE LABELED COMPOUND USING THE SAME

(71) Applicants: NIHON MEDI-PHYSICS CO., LTD., Koto-ku, Tokyo (JP); TOKYO INSTITUTE OF TECHNOLOGY, Meguro-ku, Tokyo (JP)

(72) Inventors: Masahito Toyama, Tokyo (JP); Masato Kiriu, Tokyo (JP); Hiroshi Tanaka, Tokyo (JP)

(73) Assignees: NIHON MEDI-PHYSICS CO., LTD., Koto-Ku, Tokyo (JP); TOKYO INSTITUTE OF TECHNOLOGY, Meguro-Ku, Tokyo (JP)

( * ) Notice: Subject to any disclaimer, the term of this patent is extended or adjusted under 35 U.S.C. 154(b) by 0 days.

(21) Appl. No.: 15/254,090

(22) Filed: Sep. 1, 2016

(65) Prior Publication Data
US 2017/0066748 A1   Mar. 9, 2017

(30) Foreign Application Priority Data
Sep. 8, 2015   (JP) .................. 2015-176566

(51) Int. Cl.
| | | |
|---|---|---|
| *C07D 405/06* | (2006.01) | |
| *C07D 233/86* | (2006.01) | |
| *A61K 51/04* | (2006.01) | |
| *C07B 59/00* | (2006.01) | |

(52) U.S. Cl.
CPC ........ *C07D 405/06* (2013.01); *A61K 51/0453* (2013.01); *C07B 59/00* (2013.01); *C07B 2200/05* (2013.01); *Y02P 20/55* (2015.11)

(58) Field of Classification Search
CPC ............................ C07D 405/06; C07D 233/86
USPC ....................................................... 548/311.1
See application file for complete search history.

(56) References Cited

FOREIGN PATENT DOCUMENTS

| CA | 2849278 A1 | * | 3/2013 | ........... C07D 233/91 |
|---|---|---|---|---|
| EP | 2759538 A1 | | 7/2014 | |
| JP | 2015054840 A | * | 3/2015 | |
| WO | WO 2009/127372 A1 | | 10/2009 | |
| WO | WO-2009127372 A1 | * | 10/2009 | ............. C07B 59/00 |

OTHER PUBLICATIONS

Translation of the claims in the Japanese Publication JP-2015054840-A. (Year: 2015).*
Translation of the specification in the Japanese Publication JP-2015054840-A. (Year: 2015).*
Chul-Hee Cho, et al.: "Nickel-Catalyzed Cross-Coupling of Neopentyl Arenesulfonates with Methyl and Primary Alkylmagnesium Bromides," The Journal of Organic Chemistry, vol. 70, No. 4, Feb. 1, 2005, pp. 1482-1485.
Extended Search Report issued by the European Patent Office in corresponding European Patent Application No. 16186503.5 on Jan. 26, 2017 (5 pages).
Communication pursuant to Article 94(3) EPC issued by the European Patent Office in corresponding European Patent Application No. 16186503.5-1451 on Dec. 21, 2017 (3 pages).

* cited by examiner

*Primary Examiner* — Matthew P Coughlin
*Assistant Examiner* — Sagar Patel
(74) *Attorney, Agent, or Firm* — Buchanan, Ingersoll & Rooney PC

(57) ABSTRACT

There is provided a labeling precursor compound represented by the following general formula (2):

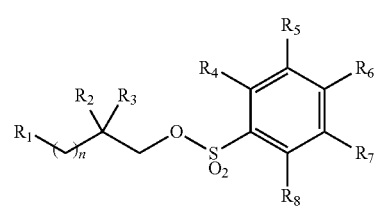

wherein $R_1$ represents an alkynyl group, an alkynyloxy group, an azide group, an azidoalkyl group, an arylazide group, a monocyclic or condensed polycyclic aryl group or a nitrogen-containing heterocycle; $R_2$ and $R_3$ each independently represent an alkyl group or a hydroxyalkyl group which hydroxy group may be protected with a protecting group, and n is an integer of 1 or 2; $R_6$ represents an alkyl group or —$CONR_{11}R_{12}$ wherein $R_{11}$ and $R_{12}$ each independently represent an alkyl group or a monocyclic or condensed polycyclic aryl group; and $R_4$, $R_5$, $R_7$ and $R_8$ each independently represent a hydrogen atom, an alkyl group or an alkoxy group.

7 Claims, No Drawings

RADIOACTIVE FLUORINE LABELING PRECURSOR COMPOUND AND METHOD FOR MANUFACTURING RADIOACTIVE FLUORINE LABELED COMPOUND USING THE SAME

This application is based on Japanese patent application No. 2015-176566, the content of which are incorporated hereinto by reference.

TECHNICAL FIELD

The present invention relates to a novel radioactive fluorine-labeling precursor compound, and a method for manufacturing a radioactive fluorine-labeled compound using the precursor compound.

BACKGROUND ART

The radioactive fluorine-labeling reaction has hitherto been often performed by a nucleophilic substitution reaction in which a compound S-L comprising a target substrate S and a leaving group L bonded to a fluorine-labeling site of the target substrate S is prepared as a labeling precursor compound, and then is allowed to react with radioactive fluoride ion X. In general, this reaction is performed by using a small amount of radioactive fluoride ion X for a large amount of the labeling precursor compound. Consequently, purification of the resultant radioactive fluorine-labeled compound is usually performed by separation from a large amount of the unreacted labeling precursor compound by use of HPLC method.

However, the HPLC method is cumbersome and takes time, thereby causing a factor of degradation of yield of the target compound in consideration of the half-life of radioactive fluorine of 110 minutes. As an alternative strategy needing no HPLC purification, International Publication No. WO 2009/127372 has proposed the following strategy: the portion L of the compound S-L is modified with a compound M to prepare a compound S-L-M as a labeling precursor compound; and the compound S-L-M is allowed to react with radioactive fluoride ion X to produce a radioactive fluorine-labeled compound S-X and a leaving group L-M so that the radioactive labeled compound S-X containing no M can be easily separated from the leaving group L-M and the unreacted labeling precursor compound S-L-M both of which contain M.

Disclosure of Invention

However, the method described in International Publication No. WO 2009/127372 is based on the concept that after the radioactive fluorination reaction, an active group immobilized on a resin is allowed to chemically act on M of the precursor compound. Accordingly, the above-described method suffers from the problems that, for example, radioactive fluorination conversion rate is adversely affected, preparation of a resin involving an operation such as introduction of a specific active group is required, and a further addition of the reaction conditions such as heating or addition of a reagent(s) after the radioactive fluorination reaction is required.

The present invention enables separation and purification of radioactive fluorine-labeled compounds from unreacted precursor compounds after radioactive fluorination reaction by a simple purification method with radioactive fluorination conversion rate being maintained at the same level as conventional methods.

The present inventors made a diligent study in order to solve the above-described problems, and consequently have completed the present invention by finding out that introducing a hydrophobic tag into the benzene ring of a leaving group formed of a benzenesulfonyloxy group enables radioactive fluorine-labeled compounds to be separated and purified from unreacted precursor compounds after radioactive fluorination reaction by a simple purification method with radioactive fluorination conversion rate being maintained at the same level as conventional methods.

According to an aspect of the present invention, there is provided a labeling precursor compound of a radioactive fluorine-labeled compound represented by the following general formula (1):

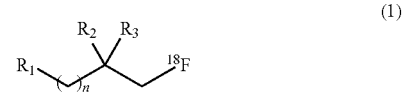

wherein $R_1$ represents an alkynyl group, an alkynyloxy group, an azide group, an azidoalkyl group, an arylazide group, a substituted or unsubstituted monocyclic or condensed polycyclic aryl group, or a substituted or unsubstituted nitrogen-containing heterocycle; $R_2$ and $R_3$ each independently represent an alkyl group having 1 to 6 carbon atoms, or a hydroxyalkyl group having 1 to 6 carbon atoms which hydroxy group may be protected with a protecting group; and n is an integer of 1 or 2, which is represented by the following general formula (2):

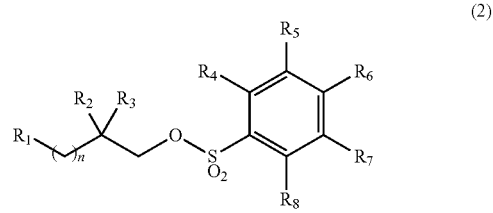

wherein $R_1$, $R_2$, $R_3$ and n are the same as those in the above-described general formula (1); $R_6$ represents an alkyl group having 4 to 24 carbon atoms, or $-CONR_{11}R_{12}$ wherein $R_{11}$ and $R_{12}$ each independently represent an alkyl group having 1 to 24 carbon atoms, or a substituted or unsubstituted monocyclic or condensed polycyclic aryl group; and $R_4$, $R_5$, $R_7$ and $R_8$ each independently represent a hydrogen atom, an alkyl group having 1 to 4 carbon atoms, or an alkoxy group having 1 to 4 carbon atoms.

According to another aspect of the present invention, there is provided a method for producing a radioactive fluorine-labeled compound, which comprises a step of allowing the above-identified labeling precursor compound to react with [$^{18}$F]fluoride ion, whereby a radioactive fluorine-labeled compound represented by the above-described general formula (1) is obtained.

According to the present invention, a compound represented by the above-described general formula (2), namely, a compound in which a hydrophobic substituent is introduced into the benzene ring of the benzenesulfonyloxy leaving group is used as the labeling precursor compound for radioactive fluorine-labeling reaction, and hence, the radioactive fluorine-labeled compound can be separated and purified from the unreacted precursor compound after radioactive fluorination reaction by a simple purification method with radioactive fluorination conversion rate being maintained at the same level as conventional methods.

DETAILED DESCRIPTION OF EMBODIMENTS

1. Radioactive Fluorine-Labeling Precursor Compound

The radioactive fluorine-labeling precursor compound of the present invention is a precursor compound of a radioactive fluorine-labeled compound represented by the above-described general formula (1), and has the structure shown in the above-described general formula (2). The labeling precursor compound is designed in such a way that the difference (C log $P_{(2)}$–C log $P_{(1)}$) between the C log P (C log $P_{(1)}$) of the radioactive fluorine-labeled compound represented by the general formula (1) and the C log P (C log $P_{(2)}$) of the precursor compound represented by the general formula (2) is preferably 1 or more, more preferably 3 or more, furthermore preferably 6 or more and particularly preferably 8 or more. The upper limit is not particularly limited, but the above-mentioned C log P difference (C log $P_{(2)}$–C log $P_{(1)}$) is preferably 50 or less, and is more practically 30 or less in consideration of solubility of the precursor compound in a reaction mixture. In this way, after the radioactive fluorine-labeling reaction, the unreacted precursor compound and the targeted radioactive fluorine-labeled compound can be separated from each other by a simple column chromatography such as a reverse phase cartridge column in a simple manner and in a short time.

In the present invention, the alkynyl group of $R_1$ is preferably a terminal alkynyl group which has a triple bond at the terminal thereof, and more preferably a terminal alkynyl group having 2 to 10 carbon atoms, including, for example, ethynyl group and 2-propynyl group.

In the present invention, the alkynyloxy group of $R_1$ is preferably a terminal alkynyloxy group which has a triple bond at the terminal thereof, and more preferably a terminal alkynyloxy group having 2 to 10 carbon atoms, including, for example, ethynyloxy group and 2-propynyloxy group.

In the present invention, the azidoalkyl group of $R_1$ is preferably a terminal azidoalkyl group which has an azide group at the terminal thereof, and more preferably a terminal azidoalkyl group having 1 to 10 carbon atoms, including, for example, azidomethyl group and azidoethyl group.

In the present invention, the arylazide group of $R_1$ includes, for example, phenylazide group and benzylazide group.

In the present invention, the monocyclic aryl group of $R_1$ includes phenyl group, and the condensed polycyclic aryl group of $R_1$ includes naphthyl group and anthracenyl group. Hydrogen atoms of these aryl groups may be substituted with, for example, an alkyl group, alkoxy group or halogen atom.

In the present invention, examples of the nitrogen-containing heterocycle of $R_1$ include a saturated or unsaturated 4- to 7-membered heterocyclic compound having 1 to 3 nitrogen atoms in the ring. Preferable among these are 5- or 6-membered rings containing 1 to 3 nitrogen atoms in the ring. Specific examples of the 6-membered ring include pyridine, piperidine, pyrimidine, pyrazine and pyridazine. Specific examples of the 5-membered ring include imidazole, imidazoline, imidazolidine, pyrazole, pyrazoline, pyrazolidine, imidazoline and triazole. In these nitrogen-containing heterocycles, hydrogen atoms bonded to carbon atoms in the ring may be substituted with a group selected from the group consisting of nitro group, amino group, alkyl group having 1 to 4 carbon atoms and hydroxyalkyl group having 1 to 4 carbon atoms. These nitrogen-containing heterocycles are each preferably bonded via a nitrogen atom thereof to the methylene group to which $R_1$ of the above-described general formula (1) or (2) is bonded.

In the present invention, the alkyl group having 1 to 6 carbon atoms of $R_2$ or $R_3$ may be a straight chain or branched chain, including, for example, methyl group, ethyl group, propyl group, isopropyl group, butyl group, sec-butyl group, isobutyl group, t-butyl group, pentyl group, neo-pentyl group and hexyl group.

In the present invention, the hydroxyalkyl group having 1 to 6 carbon atoms of $R_2$ which hydroxy group may be protected can be represented by —$(C_mH_{2m})OR_9$. The hydroxyalkyl group having 1 to 6 carbon atoms of $R_3$ which hydroxy group may be protected can be represented by —$(C_mH_{2m})OR_{10}$. Here, m in —$(C_mH_{2m})OR_9$ and m in —$(C_mH_{2m})OR_{10}$ are each independently an integer of 1 to 6, and $R_9$ and $R_{10}$ are each independently a hydrogen atom or a protecting group for a hydroxy group. The hydroxyalkyl group of $R_2$ or $R_3$ may be a straight chain or branched chain, and m is preferably 1 or 2.

In the present invention, as the protecting group for a hydroxy group, represented by $R_9$ or $R_{10}$, those described in Greene's Protective Groups in Organic Synthesis (5th edition) can be used, including, for example, trityl group, monomethoxytrityl group, dimethoxytrityl group, trimethoxytrityl group, methoxymethyl group, 1-ethoxyethyl group, methoxyethoxymethyl group, benzyl group, p-methoxybenzyl group, 2-tetrahydropyranyl group, trimethylsilyl group, triethylsilyl group, t-butyldimethylsilyl group, t-butyldiphenylsilyl group, acetyl group, propanoyl group, pivaloyl group, palmitoyl group, dimethylaminomethylcarbonyl group, alanyl group, 2,2,2-trichloroethoxycarbonyl group, benzoyl group and allyloxycarbonyl group. $R_9$ and $R_{10}$ may together be a protecting group for a diol; for example, $R_9$ and $R_{10}$ may together represent a methylene group, a 1-methylethan-1,1-diyl group, an ethan-1,1-diyl group, or a 1-phenylmethan-1,1-diyl group thereby forming a 1,3-dioxane ring. Among these, $R_9$ and $R_{10}$ preferably represent an acetonide group in which $R_9$ and $R_{10}$ together represent a 1-methylethane-1,1-diyl group, thereby forming a 1,3-dioxane ring.

In the present invention, the alkyl group having 4 to 24 carbon atoms of $R_6$ may be a straight chain or branched chain, and is preferably a straight-chain and more preferably a straight-chain alkyl group having 8 to 16 carbon atoms. In the group represented by —$CONR_{11}R_{12}$ of $R_6$, examples of the alkyl groups of $R_{11}$ and $R_{12}$ include a straight-chain or branched-chain alkyl group having 1 to 24 carbon atoms; $R_{11}$ and $R_{12}$ are each preferably a straight-chain alkyl group. Examples of the monocyclic aryl group of $R_{11}$ and $R_{12}$ include phenyl group; and examples of the condensed polycyclic aryl group of $R_{11}$ and $R_{12}$ include naphthyl group and anthracenyl group. Hydrogen atoms of the aryl group may be substituted with, for example, an alkyl group, alkoxy group or halogen atom; the aryl group is more preferably a condensed polycyclic aryl group. $R_{11}$ and $R_{12}$ may be the same or different from each other; $R_{11}$ and $R_{12}$ are preferably the same groups.

In the present invention, examples of the alkyl groups of $R_4$, $R_5$, $R_7$ and $R_8$ include a straight-chain or branched-chain alkyl group having 1 to 4 carbon atoms; examples of the alkoxy groups of $R_4$, $R_5$, $R_7$ and $R_8$ include a straight-chain or branched chain alkoxy group having 1 to 4 carbon atoms; $R_4$, $R_5$, $R_7$ and $R_8$ are each preferably a hydrogen atom.

The radioactive fluorine-labeling precursor compound of the present invention is preferably represented by the general formula (2) in which $R_6$ represents a straight-chain alkyl group having 4 to 24 carbon atoms or $-CONR_{11}R_{12}$; $R_4$, $R_5$, $R_7$ and $R_8$ each represent a hydrogen atom; and when $R_6$ is $-CONR_{11}R_{12}$, $R_{11}$ and $R_{12}$ are more preferably each independently a straight-chain alkyl group having 1 to 24 carbon atoms or a substituted or unsubstituted condensed polycyclic aryl group.

As shown in the following SCHEME 1, the radioactive fluorine-labeling precursor compound of the present invention can be produced, for example, by allowing a sulfonyl fluoride corresponding to the leaving group and diazabicycloundecene (DBU) to act on a trimethylsilyl ether in which TMSO (trimethylsiloxy) group is introduced into the site into which a radioactive fluorine atom is to be introduced. In the following SCHEME 1, $R_1$ to $R_8$ are the same as described above in relation of formula (1) and formula (2).

SCHEME 1

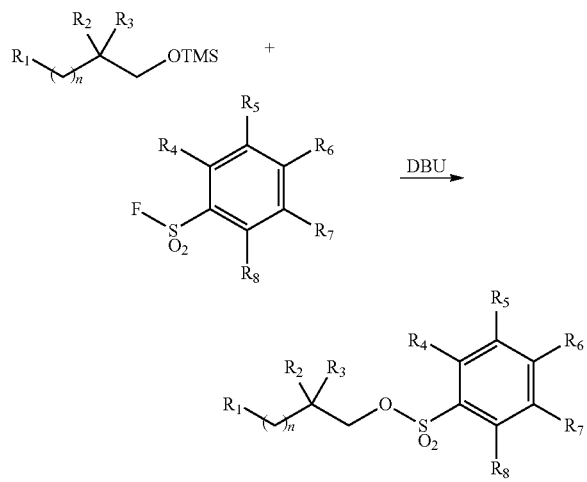

A preferred embodiment of the radioactive fluorine-labeling precursor compound of the present invention is a compound represented by the above-described general formula (2) in which $R_1$ represents a substituted or unsubstituted nitrogen-containing heterocycle, which is specifically a group represented by the following formula (3).

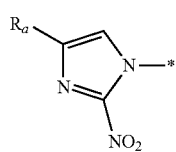
(3)

In formula (3), $R_a$ is a hydrogen atom, methyl group or hydroxymethyl group. In addition, * (asterisk) indicates the bonding site. As an example of the radioactive fluorine-labeling precursor compound of the present invention, mention may be made of a compound represented by the following formula (2-1) is quoted.

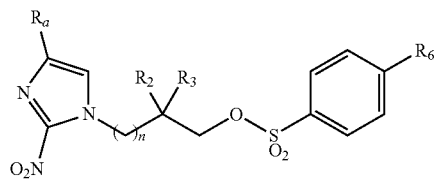
(2-1)

wherein $R_2$, $R_3$ and n are the same as those in the above-described general formula (1); $R_6$ is the same as that in the above-described general formula (2), and $R_a$ is the same as that in the above-described formula (3)).

2. Method for Producing Radioactive Fluorine-Labeled Compound Using Radioactive Fluorine-Labeling Precursor Compound According to the present invention, the radioactive fluorine-labeled compound represented by the above-described general formula (1) can be produced by subjecting the radioactive fluorine-labeling precursor compound represented by the above-described general formula (2) to a step of allowing it to react with [$^{18}$F]fluoride ion (radioactive fluorine-labeling reaction step).

The radioactive fluorine-labeling reaction is preferably performed in an inert solvent in the presence of a base. Specifically, a compound of the above-described general formula (1) can be obtained by a reaction in an appropriate solvent such as an aprotic solvent including acetonitrile, N,N-dimethylformamide or dimethyl sulfoxide at a temperature of 20 to 120° C. using, as [$^{18}$F]fluoride ion, an aqueous solution of [$^{18}$F]fluoride ion produced from [$^{18}$O]water with a cyclotron and using, as a base, for example, tetrabutylammonium or potassium carbonate/kryptofix 222. This radioactive fluorine-labeling reaction can be performed in a synthesis apparatus equipped with a reaction vessel and a shield. This synthesis apparatus may be an automatic synthesis apparatus allowing all the steps involved to be automated.

In the above-described reaction step, the target compound of the general formula (1) is produced together with by-products such as the unreacted precursor compound (namely, the compound represented by formula (2)) and the OH-form represented by the following formula (3).

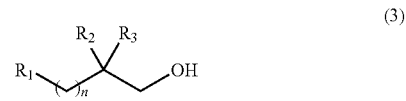
(3)

wherein $R_1$, $R_2$, $R_3$ and n are the same as in the above-described general formula (1).

Purification of the target compound of the above-described general formula (1) can be performed according to a solid phase extraction method using a reverse phase cartridge column. Specifically, the unreacted precursor compound, namely, the compound represented by the above-described general formula (2) is usually higher in lipophilicity, in other words, higher in hydrophobicity than the target compound of the above-described general formula (1). Accordingly, the target compound of the above-described general formula (1) can be separated and collected by a process utilizing the difference in hydrophobicity for example, a process in which the reaction mixture obtained in the radioactive fluorine-labeling reaction step is added to a reverse phase cartridge column packed with octadecyl silica gel or the like to separate [$^{18}$F]fluoride ion, and then an appropriate elution solvent is allowed to pass through the column so as to elute the target compound of the above-described general formula (1). Examples of the elution solvent include: water-soluble solvents such as acetonitrile, ethanol, t-butanol and methanol, or mixed liquids of these solvents and water. The collected target compound of the above-described general formula (1) may be, if necessary, subjected to deprotection or the like to be converted into a desired compound.

For example, the compound of the above-described general formula (1) in which $R_1$ represents an alkynyl group or alkynyloxy group makes it possible to introduce radioactive fluorine into a biological molecule such as peptide and protein having an azide group introduced thereinto if it is subjected to a cycloaddition reaction using a copper catalyst with the biological molecule after the radioactive fluorine-labeling reaction step using the corresponding precursor compound.

In addition, for example, the compound of the above-described general formula (1) in which $R_1$ represents an azide group, azidoalkyl group or arylazide group makes it possible to introduce radioactive fluorine into a biological molecule such as peptide and protein having a terminal alkyne introduced thereinto if it is similarly subjected to a cycloaddition reaction using a copper catalyst with the biological molecule after the radioactive fluorine-labeling reaction step using the corresponding precursor compound.

EXAMPLES

Hereinafter, the present invention is described more specifically by way of Examples; however, the present invention is not limited only to following Examples.

It is to be noted that in the following Examples, the names of the individual compounds used in experiments are defined as shown in Table 1.

TABLE 1

| Compound name | Chemical formula | |
|---|---|---|
| Precursor compound 1 | [structure] | R = $C_{12}H_{25}$ |
| Precursor compound 2 | | R = $C_8H_{17}$ |
| Precursor compound 3 | | R = $C_4H_9$ |
| Precursor compound 4 | [structure] | R = [9-anthracenyl] |
| Precursor compound 5 | [structure] | R = $C_{12}H_{25}$ |
| Precursor compound 6 | [structure] | |

TABLE 1-continued

| Compound name | Chemical formula | |
|---|---|---|
| Precursor compound 7 Precursor compound 8 | (structure) | $R = C_{18}H_{37}$ $R = C_{22}H_{45}$ |

In the Examples, the molecular structure of the individual compounds was identified on the basis of NMR spectra. As the NMR apparatus, JNM-ECP-400 (manufactured by JEOL Ltd.) was used; as the solvent, deuterated chloroform was used. $^1$H-NMR was measured at a resonance frequency of 400 MHz, and the signal δ7.24 of deuterated chloroform was used as the reference. $^{13}$C-NMR was measured at a resonance frequency of 100 MHz. All the chemical shifts are given in terms of ppm on the delta scale (δ); the fine splittings of the signals are indicated using abbreviations (s: singlet, d: doublet, t: triplet, dd: double doublet, dt: double triplet, dq: double quartet, ddt: double double triplet, m: multiplet, br: broad).

Hereinafter, in the Examples, "room temperature" means 25° C.

In the synthesis example of each compound, each step in the compound synthesis was, if necessary, repeated two or more times, to secure the amounts required when used as intermediates or the like in other syntheses.

Example 1: Synthesis of Precursor Compound 1

According to the following scheme, {2,2-dimethyl-5-[(2-nitro-1H-imidazol-1-yl)methyl]-1,3-dioxan-5-yl}methyl 4-(didodecylcarbamoyl)benzenesulfonate (precursor compound 1) was synthesized.

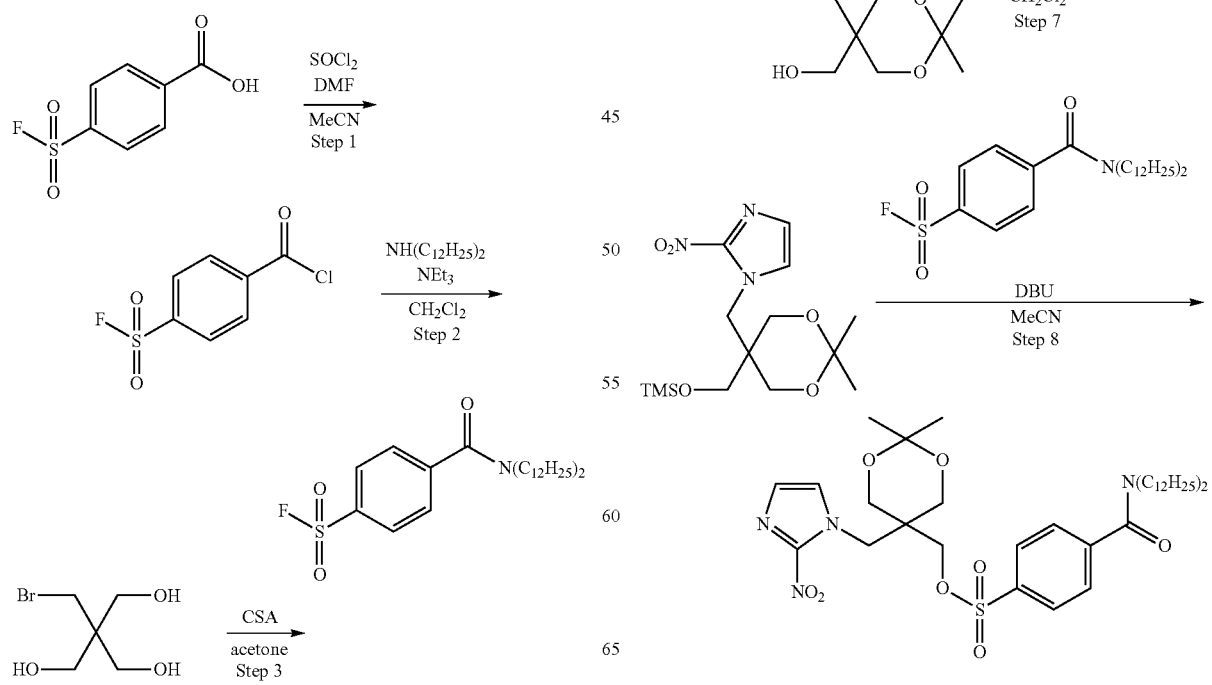

Step 1: Synthesis of 4-(fluorosulfonyl)benzoyl chloride 4-(Fluorosulfonyl)benzoyl acid (500 mg, 2.45 mmol) was dissolved in chloroform (7.4 mL), and thionyl chloride (0.711 mL, 9.8 mmol) and dimethylformamide (0.05 mL) were added to the resulting solution, and the solution was heated at 65° C. for 5 hours. After completion of the reaction, the solvent was removed under reduced pressure to yield a crude product of 4-(fluorosulfonyl)benzoyl chloride.

Step 2: Synthesis of 4-(didodecylcarbamoyl)benzenesulfonyl fluoride

Didodecylamine (1.04 g, 2.94 mmol) was dissolved in dichloromethane (6.0 mL), triethylamine (0.683 mL, 4.9 mmol) was added to the resulting solution, the solution was cooled to 0° C., and a solution prepared by dissolving the total amount of the crude product of 4-(fluorosulfonyl)benzoyl chloride synthesized in Step 1 in dichloromethane (6.0 mL) was added dropwise to the cooled solution and stirred at 0° C. for 1.5 hours. After completion of the reaction, the reaction mixture was added to 1 mol/L hydrochloric acid, and the mixture was extracted with ethyl acetate twice. The combined extract was washed with a saturated aqueous sodium hydrogen carbonate solution and a brine, and then dried with anhydrous magnesium sulfate and then concentrated under reduced pressure, and the residue was purified by silica gel column chromatography (eluent: hexane/ethyl acetate=75/25), to yield 4-(didodecylcarbamoyl)benzenesulfonyl fluoride (1.27 g, 2.35 mmol).

$^1$H-NMR: δ 8.05 (d, 2H, J=8.2 Hz), 7.59 (d, 2H, J=8.2 Hz), 3.49 (t, 2H, J=7.8 Hz), 3.11 (t, 2H, J=7.5 Hz), 1.66 (br, 2H), 1.49 (br, 2H), 1.40-1.00 (m, 36H), 0.88 (t, 6H, J=7.8 Hz); $^{13}$C-NMR: δ 168.7, 144.6, 133.4, 133.2, 128.6, 127.7, 48.9, 44.9, 31.8, 29.5, 29.4, 29.3, 29.0, 28.6, 27.4, 27.0, 26.4, 22.6, 14.0.

Step 7: Synthesis of 2-dimethyl-5-trimethylsiloxymethyl-5-[(2-nitro-1H-imidazol-1-yl)methyl]-1,3-dioxane According to the method described in Example 1 of WO 2013/042668, Steps 3 to 6 were performed, the obtained 2,2-dimethyl-5-hydroxymethyl-5-[(2-nitro-1H-imidazol-1-yl)methyl]-1,3-dioxane (102 mg, 0.376 mmol) was dissolved in dichloromethane (1.1 mL), the resulting solution was cooled to 0° C., and then triethylamine (0.105 mL, 0.752 mmol) and trimethylsilyl chloride (57 μL) were added to the cooled solution and stirred for 1 hour. After completion of the reaction, the solvent was concentrated under reduced pressure, and the residue was performed with short silica gel column chromatography (eluent: ethyl acetate) to yield a crude product of 2,2-dimethyl-5-trimethylsiloxymethyl-5-[(2-nitro-1H-imidazol-1-yl)methyl]-1,3-dioxane.

Step 8: Synthesis of Precursor Compound 1

4-(Didodecylcarbamoyl)benzenesulfonyl fluoride (292 mg, 0.541 mmol) was dissolved in acetonitrile (1.80 mL), and while the resulting solution was being cooled to 0° C., the crude product of 2,2-dimethyl-5-trimethylsiloxymethyl-5-[(2-nitro-1H-imidazol-1-yl)methyl]-1,3-dioxane and diazabicycloundecene (135 μL, 0.902 mmol) were added dropwise to the solution and stirred at room temperature for 1 hour. After completion of the reaction, water was added to the reaction mixture, and the mixture was extracted with ethyl acetate twice. The combined extract was washed with water and a brine, then dried with anhydrous magnesium sulfate and then concentrated under reduced pressure, and the residue was purified by silica gel column chromatography (eluent: hexane/ethyl acetate=55/45), to yield the precursor compound 1 (280 mg, 0.354 mmol).

$^1$H-NMR: δ 7.91 (d, 2H, J=8.7 Hz), 7.55 (d, 2H, J=8.3 Hz), 7.21 (d, 1H, J=1.0 Hz), 7.16 (d, 1H, J=1.0 Hz), 4.74 (s, 2H), 4.01 (s, 2H), 3.72 (d, 2H, J=12.1 Hz), 3.61 (d, 2H, J=12.1 Hz), 3.49 (t, 2H, J=7.5 Hz), 3.14 (t, 2H, J=7.3 Hz), 1.70-1.60 (m, 2H), 1.54-1.44 (m, 2H), 1.40 (s, 3H), 1.37 (s, 3H), 1.40-1.05 (m, 36H), 0.88 (t, 6H, J=6.6 Hz); $^{13}$C-NMR: δ 169.2, 145.5, 143.4, 135.2, 128.6, 128.2, 127.5, 127.1, 99.1, 77.3, 77.2, 77.0, 76.7, 69.4, 62.2, 49.0, 48.8, 44.8, 38.9, 31.9, 29.6, 29.5, 29.4, 29.3, 29.1, 28.7, 27.4, 27.0, 26.5, 26.5, 24.9, 22.6, 22.1, 14.1.

Example 2: Synthesis of Precursor Compound 2

According to the following scheme, {2,2-dimethyl-5-[(2-nitro-1H-imidazol-1-yl)methyl]-1,3-dioxan-5-yl}methyl 4-(dioctylcarbamoyl)benzenesulfonate (precursor compound 2) was synthesized.

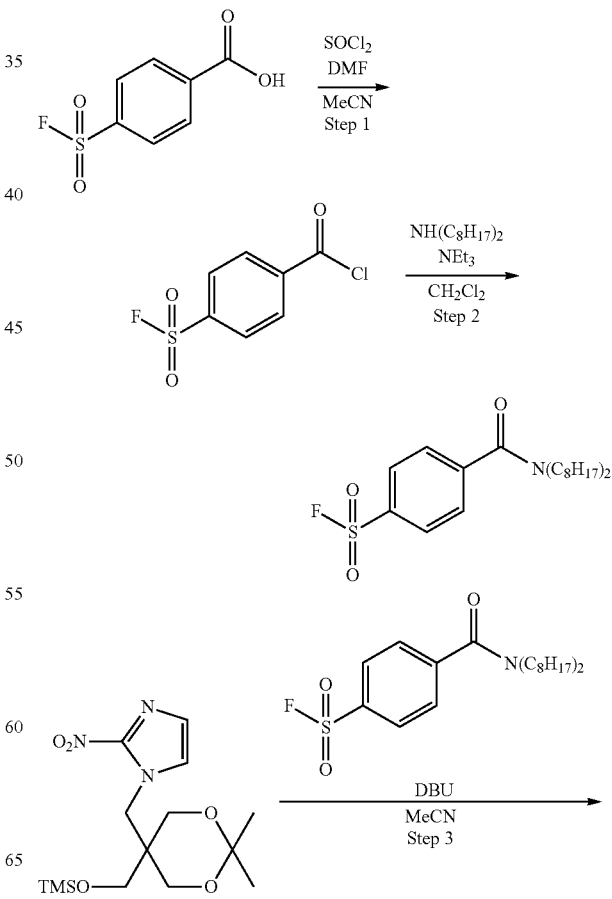

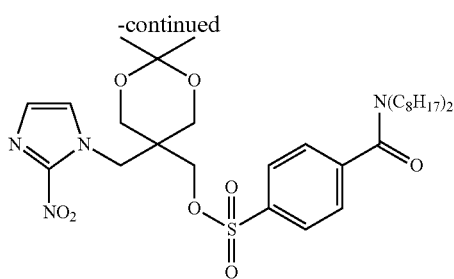

Step 2: Synthesis of 4-(dioctylcarbamoyl)benzenesulfonyl fluoride

Dioctylamine (0.71 g, 2.94 mmol) was dissolved in dichloromethane (6.0 mL), triethylamine (0.683 mL, 4.9 mmol) was added to the resulting solution, the solution was cooled to 0° C., then a solution prepared by dissolving the total amount of the crude product of 4-(fluorosulfonyl)benzoyl chloride synthesized according to the method shown in Step 1 of Example 1 in dichloromethane (6.0 mL) was added dropwise to the cooled solution and stirred at 0° C. for 1.5 hours. After completion of the reaction, the reaction mixture was added to 1 mol/L hydrochloric acid, and the mixture was extracted with ethyl acetate twice. The combined extract was washed with a saturated aqueous sodium hydrogen carbonate solution and brine, and then dried with anhydrous magnesium sulfate and then concentrated under reduced pressure, and the residue was purified by silica gel column chromatography (eluent: hexane/ethyl acetate=75/25) to yield 4-(dioctylcarbamoyl)benzenesulfonyl fluoride (0.891 g, 2.08 mmol).

$^1$H-NMR: δ 8.05 (d, 2H, J=8.5 Hz), 7.61 (d, 2H, J=8.5 Hz), 3.50 (t, 2H, J=7.5 Hz), 3.14 (t, 2H, J=7.5 Hz), 1.68 (br, 2H), 1.51 (br, 2H), 1.42-1.00 (m, 20H), 0.92-0.82 (m, 6H); $^{13}$C-NMR: δ 168.7, 144.6, 133.4, 133.1, 128.6, 127.7, 48.9, 44.9, 31.7, 31.6, 29.3, 29.1, 28.9, 28.6, 27.4, 27.0, 26.4, 22.5, 22.5, 13.95, 13.91.

Step 3: Synthesis of Precursor Compound 2

4-(Dioctylcarbamoyl)benzenesulfonyl fluoride (195 mg, 0.456 mmol) was dissolved in acetonitrile (1.50 mL), and while the resulting solution was being cooled to 0° C., the crude purified product of 2,2-dimethyl-5-trimethylsiloxymethyl-5-[(2-nitro-1H-imidazol-1-yl)methyl]-1,3-dioxane synthesized according to the method shown in Step 7 of Example 1 and diazabicycloundecene (114 μL, 0.763 mmol) were added dropwise to the solution and stirred at room temperature for 1 hour. After completion of the reaction, water was added to the reaction mixture, and the mixture was extracted with ethyl acetate twice. The combined extract was washed with water and brine, and then dried with anhydrous magnesium sulfate and then concentrated under reduced pressure, and the residue was purified by silica gel column chromatography (eluent: hexane/ethyl acetate=55/45) to yield the precursor compound 2 (221 mg, 0.326 mmol).

$^1$H-NMR: δ 7.91 (d, 2H, J=6.8 Hz), 7.54 (d, 2H, J=6.8 Hz), 7.21 (d, 1H, J=0.9 Hz), 7.17 (d, 1H, J=0.9 Hz), 4.75 (s, 2H), 4.01 (s, 2H), 3.72 (d, 2H, J=12.0 Hz), 3.61 (d, 2H, J=12.1 Hz), 3.49 (t, 2H, J=7.8 Hz), 3.14 (t, 2H, J=7.5 Hz), 1.72-1.62 (m, 2H), 1.54-1.44 (m, 2H), 1.41 (s, 3H), 1.37 (s, 3H), 1.40-1.05 (m, 20H), 0.94-0.82 (m, 6H).

Example 3: Synthesis of Precursor Compound 3

According to the following scheme, {2,2-dimethyl-5-[(2-nitro-1H-imidazol-1-yl)methyl]-1,3-dioxan-5-yl}methyl 4-(dibutylcarbamoyl)benzenesulfonate (precursor compound 3) was synthesized.

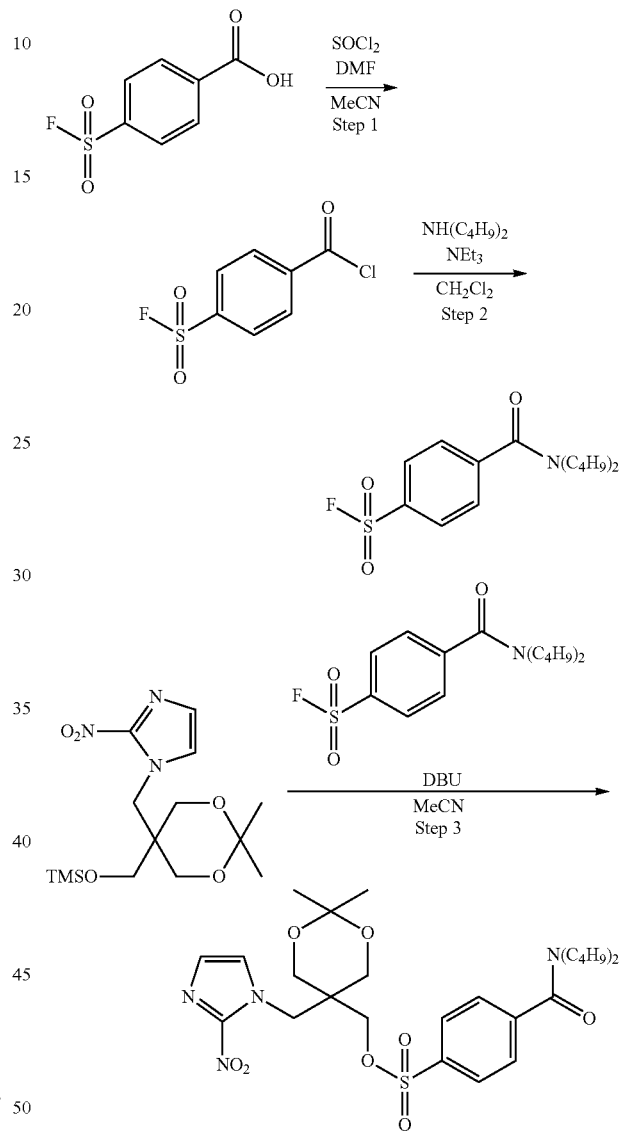

Step 2: Synthesis of 4-(butylcarbamoyl)benzenesulfonyl fluoride

Dibutylamine (0.38 g, 2.94 mmol) was dissolved in dichloromethane (6.0 mL), triethylamine (0.683 mL, 4.9 mmol) was added to the resulting solution, the solution was cooled to 0° C., and the solution prepared by dissolving the total amount of the crude product of 4-(fluorosulfonyl)benzoyl chloride synthesized according to the method shown in Step 1 of Example 1 in dichloromethane (6.0 mL) was added dropwise to the cooled solution and stirred at 0° C. for 30 minutes. After completion of the reaction, the reaction mixture was added to 1 mol/L hydrochloric acid, and the mixture was extracted with ethyl acetate twice. The combined ethyl acetate layers were washed with a saturated aqueous sodium hydrogen carbonate solution and brine, and then dried with anhydrous magnesium sulfate and then concentrated under reduced pressure, and the residue was purified by silica gel column chromatography (eluent: hexane/ethyl acetate=60/40) to yield 4-(dibutylcarbamoyl) benzenesulfonyl fluoride (0.692 g, 2.19 mmol).

$^1$H-NMR: δ 8.06 (d, 2H, J=8.5 Hz), 7.62 (d, 2H, J=8.5 Hz), 3.52 (t, 2H, J=7.5 Hz), 3.15 (t, 2H, J=7.5 Hz), 1.67 (tt, 2H, J=7.5, 7.6 Hz), 1.50 (tt, 2H, J=7.2, 7.7 Hz), 1.41 (tq, 2H, J=7.2, 7.7 Hz), 1.15 (tq, 2H, J=7.2, 7.7 Hz), 0.98 (t, 3H, J=7.2 Hz), 0.80 (t, 3H, J=7.2 Hz); $^{13}$C-NMR: δ 168.6, 144.5, 133.2, 132.9, 128.5, 127.5, 48.5, 44.4, 30.5, 29.3, 20.0, 19.5, 13.6, 13.3.

Step 3: Synthesis of Precursor Compound 3

4-(Dibutyloctylcarbamoyl)benzenesulfonyl fluoride (144 mg, 0.458 mmol) was dissolved in acetonitrile (1.50 mL), and while the resulting solution was being cooled to 0° C., the total amount of the crude product of 2,2-dimethyl-5-trimethylsiloxymethyl-5-[(2-nitro-1H-imidazol-1-yl) methyl]-1,3-dioxane synthesized according to the method shown in Step 7 of Example 1 and diazabicycloundecene (114 μL, 0.763 mmol) were added dropwise to the solution and stirred at room temperature for 1 hour. After completion of the reaction, water was added to the reaction mixture, and the mixture was extracted with ethyl acetate twice. The combined extract was washed with water and brine, and then dried with anhydrous magnesium sulfate and then concentrated under reduced pressure, and the residue was purified by silica gel column chromatography (eluent: hexane/ethyl acetate=55/45) to yield the precursor compound 3 (175 mg, 0.310 mmol).

$^1$H-NMR: δ 7.91 (d, 2H, J=7.5 Hz), 7.56 (d, 2H, J=7.5 Hz), 7.21 (d, 1H, J=1.0 Hz), 7.17 (d, 1H, J=1.0 Hz), 4.75 (s, 2H), 4.00 (s, 2H), 3.72 (d, 2H, J=12.1 Hz), 3.61 (d, 2H, J=12.1 Hz), 3.50 (t, 2H, J=7.5 Hz), 3.15 (t, 2H, J=7.8 Hz), 1.70-1.60 (m, 2H), 1.56-1.46 (m, 2H), 1.46-1.40 (m, 2H), 1.41 (s, 3H), 1.37 (m, 3H), 1.20-1.10 (m, 2H), 0.99 (t, 3H, J=7.5 Hz), 0.81 (t, 3H, J=7.5 Hz).

Example 4: Synthesis of Precursor Compound 4

According to the following scheme, {2,2-dimethyl-5-[(2-nitro-1H-imidazol-1-yl)methyl]-1,3-dioxan-5-yl}methyl 4-{(9-anthracenylmethyl) methylcarbamoyl}benzenesulfonate (precursor compound 4) was synthesized.

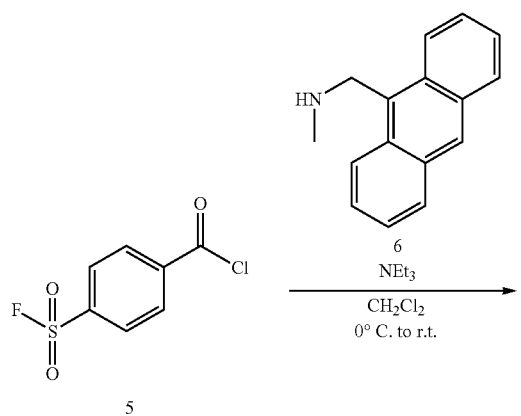

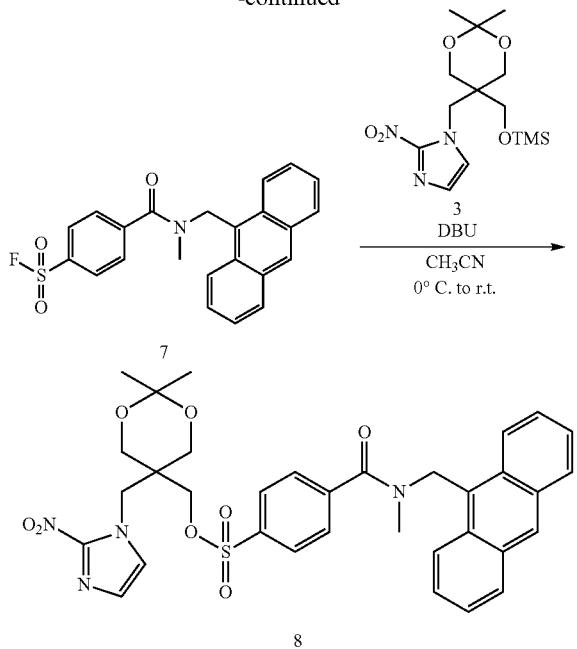

Synthesis of 4-{(9-anthracenylmethyl) methylcarbamoyl}benzenesulfonyl fluoride (Compound 7)

N-Methyl-9-anthacenylmethylamine (325 mg, 1.47 mmol) and triethylamine (340 μL, 2.45 mmol) were dissolved in dichloromethane (3.0 mL), and to the resulting solution, a dichloromethane (3.0 mL) solution of 4-(fluorosulfonyl)benzoyl acid chloride (1.23 mmol) synthesized according to the method shown in Step 1 of Example 1 was added under stirring at 0° C. The resulting mixture was stirred at room temperature for 1.5 hours, and then was supplemented with 1 mol/L cooled hydrochloric acid and extracted with ethyl acetate twice. The combined extracts were washed with brine, and then dried with magnesium sulfate and then concentrated under reduced pressure, and the residue was purified with silica gel column chromatography (eluent: toluene/ethyl acetate=60/40) to yield the compound 7 (371 mg, 0.907 mmol, yield: 74%).

$^1$H-NMR: δ 8.54 (s, 1H), 8.38 (d, 2H, J=8.7 Hz), 8.09-8.02 (m, 4.5H), 7.64-7.51 (m, 6.5H), 5.87 (s, 2H), 2.51 (s, 3H).

Synthesis of Precursor Compound 4 (Compound 8)

The compound 7 (181 mg, 0.444 mmol) and 2,2-dimethyl-5-trimethylsiloxymethyl-5-[(2-nitro-1H-imidazol-1-yl)methyl]-1,3-dioxane (compound 3, 0.370 mmol) synthesized according to the method shown in Step 7 of Example 1 were dissolved in acetonitrile (1.5 mL), and while the resulting solution was being cooled to 0° C., diazabicycloundecene (110 μL, 0.740 mmol) was added dropwise to the solution and stirred at room temperature for 1 hour. After completion of the reaction, water was added to the reaction mixture, and the mixture was extracted with ethyl acetate twice. The combined extracts were washed with brine, and then dried with magnesium sulfate, and then filtered followed by concentration under reduced pressure. Then, the residue was purified with silica gel column chromatography (eluent: toluene/ethyl acetate=60/40) to yield the precursor compound 4 (211 mg, 0.322 mmol, yield: 87%).

$^1$H-NMR: δ 8.53 (s, 1H), 8.39 (d, 1.8H, J=9.2 Hz), 8.08 (d, 2.2H, J=8.2 Hz), 7.87 (d, 2H, J=8.3 Hz), 7.62-7.51 (m, 6H), 7.19 (d, 1H, J=1.0 Hz), 7.13 (s, 1H), 5.87 (s, 2H), 4.72 (s, 2H), 3.97 (s, 2H), 3.71 (d, 2H, J=12.6 Hz), 3.59 (d, 2H, J=12.6 Hz), 2.54 (s, 3H), 1.39 (s, 3H), 1.35 (s, 3H).

Example 5: Synthesis of Precursor Compound 5

According to the following scheme, {2,2-dimethyl-5-[(2-nitro-1H-imidazol-1-yl)methyl]-1,3-dioxan-5-yl}methyl 4-dodecylbenzenesulfonate (precursor compound 5) was synthesized.

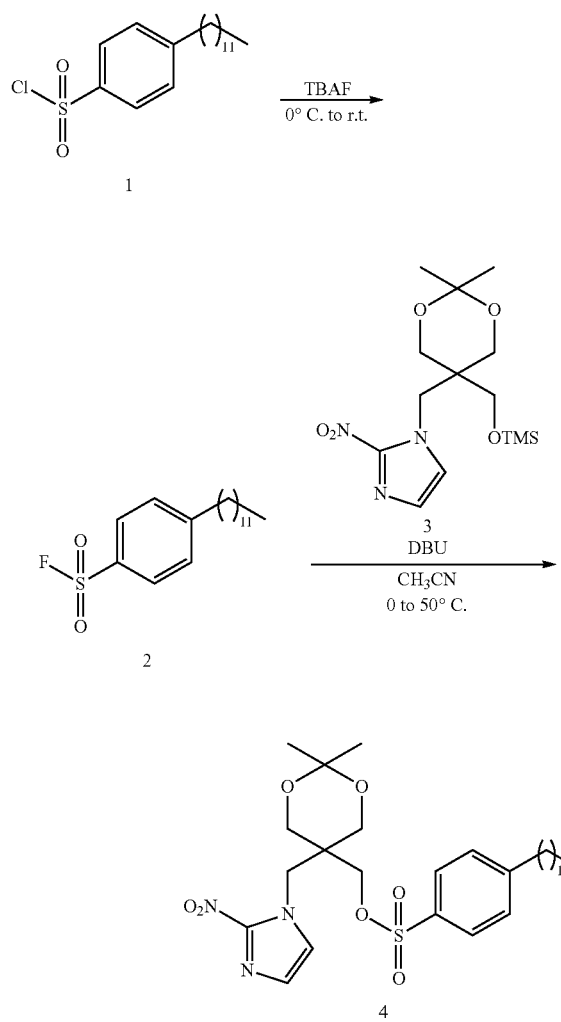

Synthesis of 4-Dodecylbenzenesulfonyl Fluoride (Compound 2)

To a dichloromethane solution of 4-dodecylbenzenesulfonyl chloride (253 mg, 0.733 mmol), tetra-n-butylammonium fluoride (1.00 mol/L tetrahydrofuran solution) (1.47 mL, 1.47 mmol) was added under stirring. After the mixture was stirred for 1 hour, water was added to the mixture while the mixture was being cooled, and then the mixture was extracted with ethyl acetate twice. The combined extract was washed with brine, dried with magnesium sulfate, and then concentrated under reduced pressure; then the residue was purified with silica gel column chromatography (eluent: hexane/toluene=90/10) to yield the compound 2 (176 mg, 0.535 mmol, yield: 73%).

$^1$H-NMR: δ 7.93-7.91 (m, 2H), 7.43-7.37 (m, 2H), 2.82-2.62 (m, 1H), 1.78-0.74 (m, 24H).

Synthesis of Precursor Compound 5 (Compound 4)

To an acetonitrile (1.5 mL) solution of the compound 2 (177 mg, 0.539 mmol) and 1-[(2,2-dimethyl-5-{[(trimethylsilyl)oxy]methyl}-1,3-dioxan-5-yl)methyl]-2-nitro-1H-imidazole (compound 3) (0.449 mmol) synthesized according to the method shown in Step 7 of Example 1, diazabicycloundecene (134 μL, 0.899 mmol) was added dropwise at 0° C. under stirring. The reaction mixture was heated to 50° C. and then stirred for 3.5 hours; then water was added to the reaction mixture, and the mixture was extracted with ethyl acetate twice. The combined extract was washed with brine, dried with magnesium sulfate, and then concentrated under reduced pressure. Then, the residue was purified with silica gel column chromatography (eluent: hexane/ethyl acetate=55/45) to yield the precursor compound 5 (190 mg, 0.328 mmol, yield: 73%).

$^1$H-NMR: δ 7.79 (d, 2H, J=8.2 Hz), 7.40-7.33 (m, 2H), 7.20-7.14 (m, 2H), 4.71 (s, 2H), 3.99-3.96 (m, 2H), 3.71-3.60 (m, 2H), 2.84-2.48 (m, 1H), 1.76-0.74 (m, 24H).

Example 6: Synthesis of Precursor Compound 6

According to the following scheme, {2,2-dimethyl-5-[(2-nitro-1H-imidazol-1-yl)methyl]-1,3-dioxan-5-yl}methyl 4-(di-[(1-naphthalenyl)methyl]carbamoyl)benzenesulfonate (precursor compound 6) was synthesized.

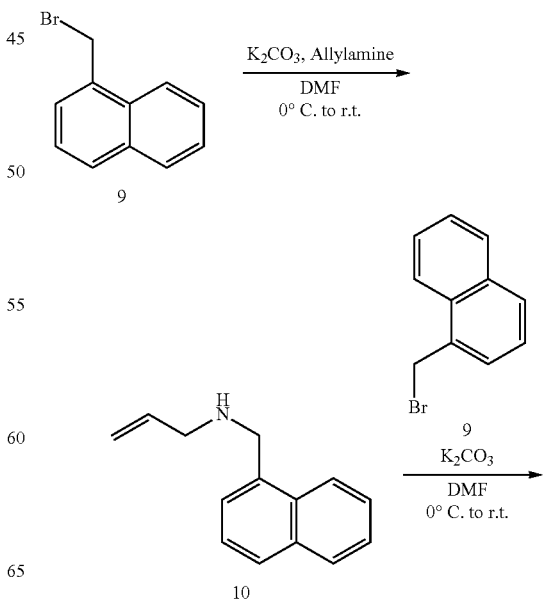

-continued

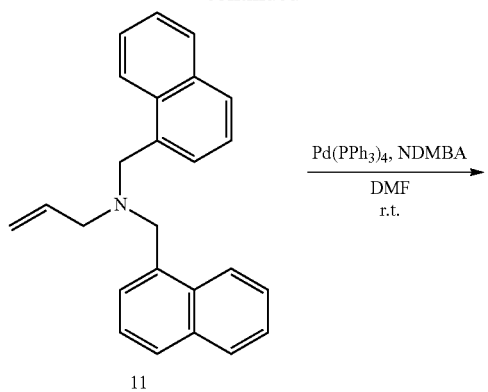

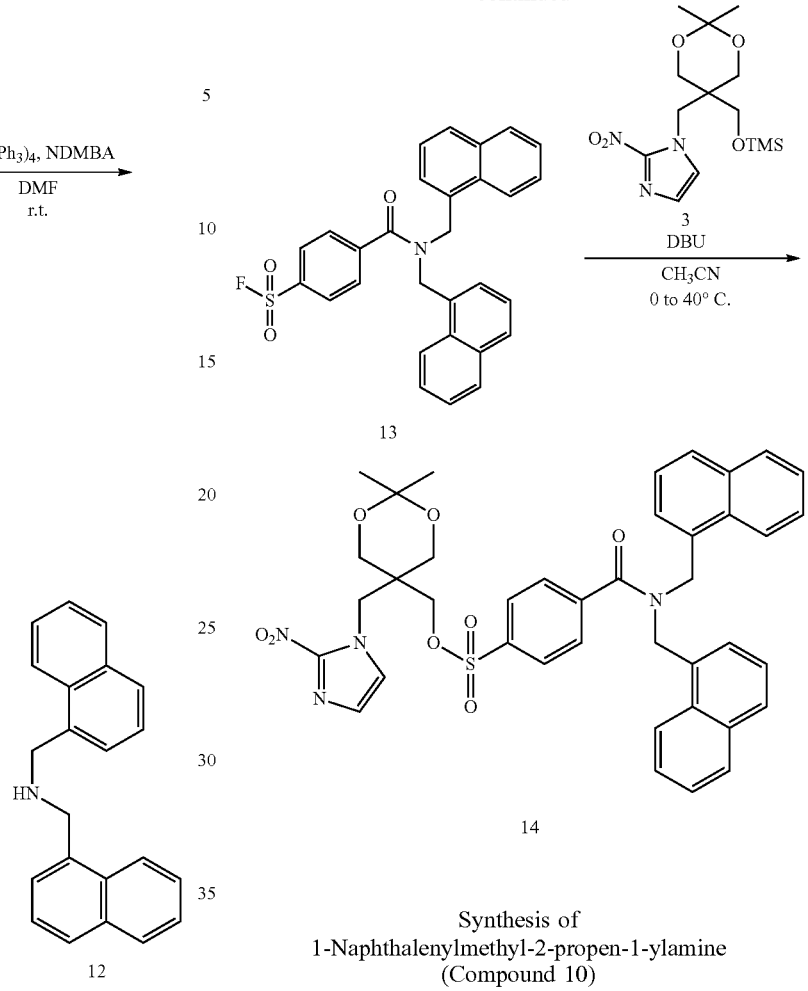

Synthesis of 1-Naphthalenylmethyl-2-propen-1-ylamine (Compound 10)

To a dimethylformamide (2.0 mL) solution of allylamine (204 μL, 2.71 mmol) and potassium carbonate (375 mg, 2.71 mmol), a dimethylformamide (3.5 mL) solution of 1-(bromomethyl)-naphthalene (compound 9) (300 mg, 1.36 mmol) was added dropwise at 0° C. under stirring. After the reaction mixture was stirred for 1 hour at room temperature, water was added to the reaction mixture, and then the mixture was extracted with ethyl acetate twice. The extracts were combined, dried with magnesium sulfate, and concentrated under reduced pressure. Then, the residue was purified with silica gel column chromatography (eluent: toluene/ ethyl acetate=60/40) to yield the compound 10 (196 mg, 0.142 mmol, yield: 73%).

$^1$H-NMR: δ 8.07 (d, 1H, J=8.2 Hz), 7.79 (d, 1H, J=7.7 Hz), 7.70 (d, 1H, J=8.2 Hz), 7.49-7.34 (m, 4H), 6.00-5.80 (m, 1H), 5.22-5.14 (m, 1H), 5.12-5.06 (m, 1H), 4.15 (s, 2H), 3.34-3.28 (m, 2H).

Synthesis of Propen-1-yl-di-[(1-naphthalenyl)methyl]amine (Compound 11)

To a dimethylformamide (8.8 mL) solution of the compound 10 (440 mg, 2.23 mmol) and potassium carbonate (336 mg, 2.43 mmol), 1-(bromomethyl)-naphthalene (448 mg, 2.03 mmol) was added dropwise at 0° C. under stirring. After the reaction mixture was stirred for 1.5 hours at room temperature, water was added to the reaction mixture, and then the mixture was extracted with ethyl acetate twice. The

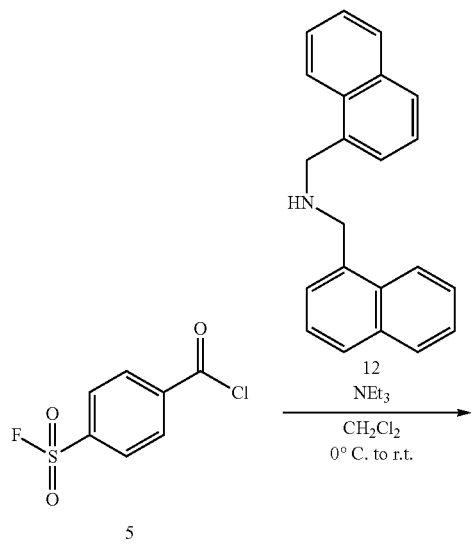

combined extract was washed with brine, dried with magnesium sulfate, and concentrated under reduced pressure. Then, the residue was purified with silica gel column chromatography (eluent: hexane/toluene=85/15) to yield the compound 11 (580 mg, 1.70 mmol, yield: 84%).

$^1$H-NMR: δ 7.98 (d, 2H, J=8.2 Hz), 7.75 (d, 2H, J=8.2 Hz), 7.68 (d, 2H, J=8.2 Hz), 7.45-7.30 (m, 6H), 7.22-7.21 (m, 2H), 6.07-5.98 (m, 1H), 5.21-5.16 (m, 2H), 3.97 (s, 4H), 3.10 (d, 2H, J=6.3 Hz).

Synthesis of di-[(1-Naphthalenyl)methyl]amine (Compound 12)

To a dimethylformamide (7.0 mL) solution of the compound 11 (481 mg, 1.43 mmol), tetrakis(triphenylphosphine)palladium (82.3 mg, 0.0712 mmol) and 1,3-dimethylbarbituric acid (668 mg, 4.28 mmol) were added dropwise at 0° C. under stirring. The reaction mixture was stirred at room temperature for 0.5 hour, then a saturated aqueous sodium hydrogen carbonate solution was added to the reaction mixture, and the mixture was extracted with ethyl acetate twice. The combined extract was washed with brine, dried with magnesium sulfate, and then concentrated under reduced pressure. Then, the residue was purified with silica gel column chromatography (eluent: hexane/ethyl acetate=80/20) to yield the compound 12 (334 mg, 1.13 mmol, yield: 79%).

$^1$H-NMR: δ 8.08-8.06 (m, 2H), 7.85-7.83 (m, 2H), 7.76 (d, 2H, J=8.2 Hz), 7.51-7.39 (m, 8H), 4.33 (s, 4H), 1.87 (s, 1H).

Synthesis of 4-(di-[(1-Naphthalenyl)methyl]carbamoyl)benzenesulfonyl Fluoride (Compound 13)

To a dichloromethane (2.0 mL) solution of the compound 12 (320 mg, 1.08 mmol) and triethylamine (280 μL, 1.96 mmol), a dichloromethane (3.0 mL) solution of the compound 5 (0.980 mmol) synthesized according to the method shown in Step 1 of Example 1 was added under stirring. After the reaction mixture was stirred at room temperature for 0.5 hour, the reaction mixture was added to 1 mol/L hydrochloric acid while being cooled, and the mixture was extracted with ethyl acetate twice. The combined extract was washed with brine, dried with magnesium sulfate, and then concentrated under reduced pressure. Then, the residue was purified with silica gel column chromatography (eluent: hexane/ethyl acetate=80/20) to yield the compound 13 (454 mg, 0.940 mmol, yield: 96%).

$^1$H-NMR: δ 8.20-8.10 (br, 1H), 7.92-7.84 (m, 6H), 7.67 (d, 2H, J=8.2 Hz), 7.64-7.30 (br, 8H), 7.22-7.12 (br, 1H), 5.39 (s, 2H), 4.71 (s, 2H).

Synthesis of Precursor Compound 6 (Compound 14)

To an acetonitrile (1.7 mL) solution of the compound 13 (211 mg, 0.436 mmol) and the compound 3 (0.397 mmol) synthesized according to Step 7 of Example 1, diazabicycloundecene (120 μL, 0.794 mmol) was added dropwise at 0° C. under stirring. After the reaction mixture was stirred at 40° C. for 1 hour, water was added to the reaction mixture, and the mixture was extracted with ethyl acetate twice. The combined extract was washed with brine, dried with magnesium sulfate and then concentrated under reduced pressure. Then, the residue was purified with silica gel column chromatography (eluent: toluene/ethyl acetate=60/40) to yield the precursor compound 6 (121 mg, 0.167 mmol, yield: 42%).

$^1$H-NMR: δ 8.16-8.08 (br, 1H,), 7.94-7.82 (m, 5H), 7.78 (d, 2H, J=7.8 Hz), 7.62-7.28 (m, 9H), 7.20-7.14 (br, 1H), 7.11 (d, 1H, J=0.9 Hz), 7.04 (d, 1H, J=0.9 Hz), 5.42-5.32 (br, 2H), 4.80-4.70 (br, 2H), 4.64 (s, 2H), 3.92 (s, 2H), 3.62 (d, 2H, J=12.6 Hz), 3.52 (d, 2H, J=12.6 Hz), 1.33 (s, 2H), 1.26 (s, 2H).

Example 7: Synthesis of Precursor Compound 7

According to the following scheme, {2,2-dimethyl-5-[(2-nitro-1H-imidazol-1-yl)methyl]-1,3-dioxan-5-yl}methyl 4-(dioctadecylcarbamoyl)benzenesulfonate (precursor compound 7) was synthesized.

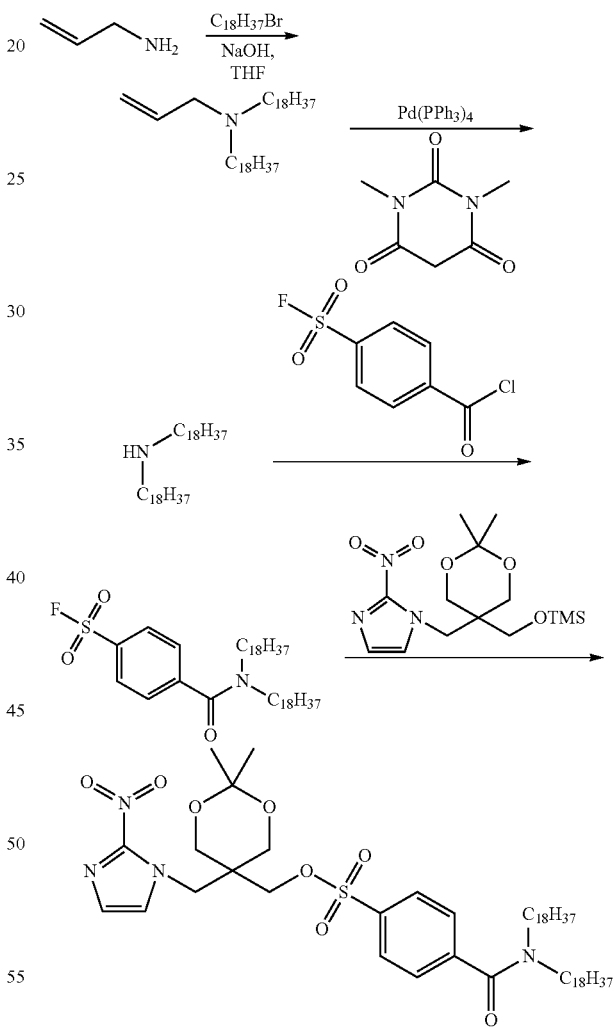

Synthesis of Dioctadecylallylamine

A tetrahydrofuran (16 mL) solution of octadecyl bromide (2.16 g, 6.47 mmol), allylamine (0.739 g, 12.9 mmol) and sodium hydroxide (0.776 g, 19.4 mmol) was stirred in a sealed tube at 120° C. for 24 hours, and then water was added to the reaction mixture, and the mixture was extracted with ethyl acetate twice. The combined extract was washed with brine, dried with magnesium sulfate, and then concentrated under reduced pressure. Then, the residue was purified with silica gel column chromatography (eluent: toluene/ethyl acetate=50/50) to yield dioctadecylallylamine (376 mg, 0.661 mmol, yield: 21%).

$^1$H-NMR: δ 5.85 (ddt, 1H, J=16.9 Hz, J=10.2 Hz, J=6.8 Hz), 5.14 (dd, 1H, J=16.9 Hz, J=1.9 Hz), 5.09 (dd, 1H, J=10.2 Hz, J=1.9 Hz), 3.07 (d, 2H, J=6.8 Hz), 2.39 (t, 4H, J=7.3 Hz), 1.46-1.38 (m, 4H), 1.34-1.18 (m, 60H), 0.88 (t, 6H, 6.3 Hz).

Synthesis of Dioctadecylamine

A methylene chloride (0.89 mL) solution of dioctadecylallylamine (99.7 mg, 0.178 mmol), tetrakispalladium (10.2 mg, 0.0088 mmol) and N,N-dimethylbarbituric acid (83.1 mg, 0.532 mmol) was stirred at room temperature for 40 minutes, then water was added to the reaction mixture, and the mixture was extracted with chloroform twice. The combined extract was washed with brine, dried with magnesium sulfate, and then concentrated under reduced pressure. The obtained residue was used in the following reaction.

Synthesis of
4-(Dioctadecylcarbamoyl)benzenesulfonyl Fluoride

The total amount of dioctadecylamine was dissolved in tetrahydrofuran (0.7 mL), triethylamine (0.298 mL, 2.01 mmol) was added to the resulting solution, and the solution was cooled to 0° C. A solution prepared by dissolving the total amount of the crude purified product of 4-(fluorosulfonyl)benzoyl acid chloride synthesized according to the method shown in Step 1 of Example 1 in dichloromethane (2.5 mL) was added dropwise to the cooled solution and stirred at 0° C. for 1.5 hours. After completion of the reaction, the reaction mixture was added to 1 mol/L hydrochloric acid, and the mixture was extracted with methylene chloride twice. The combined extract was washed with a saturated aqueous sodium hydrogen carbonate solution and brine, then dried with anhydrous magnesium sulfate, and then concentrated under reduced pressure. The residue was purified by silica gel column chromatography (eluent: hexane/diethyl ether=80/20), and the obtained compound was purified by using a molecular sieve column to yield 4-(dioctadecylcarbamoyl)benzenesulfonic acid fluoride (0.0901 g, 0.127 mmol).

$^1$H-NMR: δ 8.05 (d, 2H, J=8.7 Hz), 7.59 (d, 2H, J=8.7 Hz), 3.49 (t, 2H, J=7.8 Hz), 3.12 (t, 2H, J=7.7 Hz), 1.72-1.60 (m, 2H), 1.54-1.44 (m, 2H), 1.40-1.04 (m, 60H), 0.88 (t, 6H, J=6.8 Hz).

Synthesis of Precursor Compound 7

To a methylene chloride (0.90 mL) solution of 4-(dioctadecylcarbamoyl)benzenesulfonic acid fluoride (130 mg, 0.183 mmol) and the total amount of the crude purified product (0.166 mmol) of 2,2-dimethyl-5-trimethylsiloxymethyl-5-[(2-nitro-1H-imidazol-1-yl)methyl]-1,3-dioxane synthesized according to Step 7 of Example 1, diazabicycloundecene (50 μL, 0.326 mmol) was added dropwise at 0° C. under stirring. After the reaction mixture was stirred at room temperature for 1 hour, water was added to the reaction mixture, and the mixture was extracted with ethyl acetate twice. The combined extract was washed with brine, dried with magnesium sulfate, and then concentrated under reduced pressure. Then, the residue was purified with silica gel column chromatography (eluent: hexane/ethyl acetate=60/40) to yield the precursor compound 7 (37.6 mg, 0.399 mmol, yield: 24%).

$^1$H-NMR: δ 7.90 (d, 2H, J=8.2 Hz), 7.54 (d, 2H, J=8.2 Hz), 7.20 (s, 1H), 7.16 (s, 1H), 4.74 (s, 2H), 4.01 (s, 2H), 3.72 (d, 2H, J=12.1 Hz), 3.61 (d, 2H, J=12.1 Hz), 3.48 (t, 2H, J=7.8 Hz), 3.14 (t, 2H, J=7.7 Hz), 1.70-1.60 (m, 2H), 1.58-1.04 (m, 62H), 0.88 (t, 6H, J=6.8 Hz).

Example 8: Synthesis of Precursor Compound 8

According to the following scheme, {2,2-dimethyl-5-[(2-nitro-1H-imidazol-1-yl)methyl]-1,3-dioxan-5-yl}methyl 4-(didocosylcarbamoyl)benzenesulfonate (precursor compound 8) was synthesized.

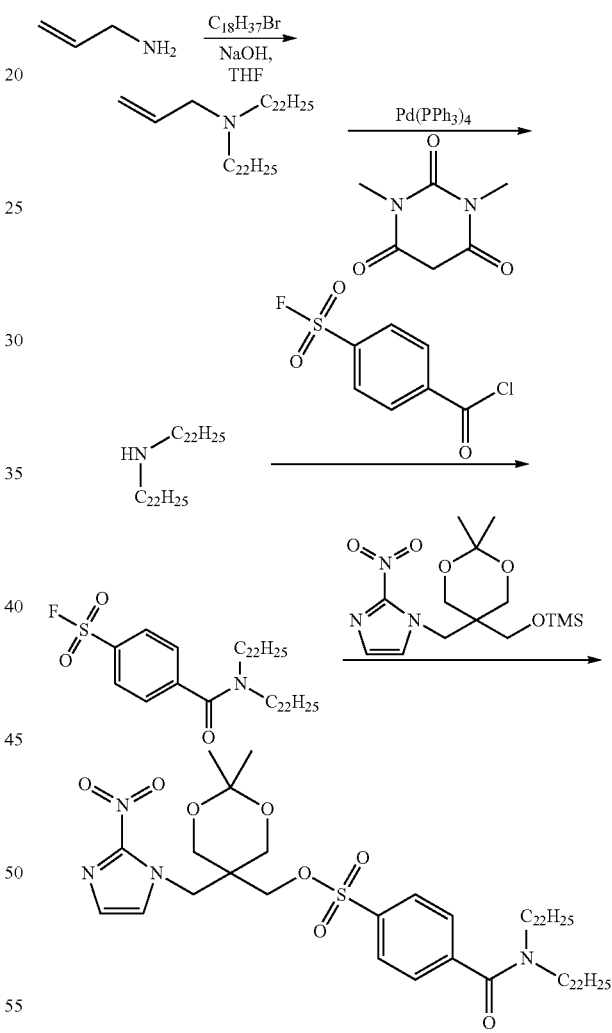

Synthesis of N,N-Didocosyl allylamine

A tetrahydrofuran (11.5 mL) solution of docosyl bromide (1.50 g, 3.85 mmol), allylamine (0.439 g, 7.70 mmol) and sodium hydroxide (0.426 g, 11.5 mmol) was stirred in a sealed tube at 120° C. for 24 hours, then water was added to the reaction mixture, and the mixture was extracted with ethyl acetate twice. The combined extract was washed with brine, dried with magnesium sulfate, and then concentrated under reduced pressure. Then, the residue was purified with silica gel column chromatography (eluent: toluene/ethyl acetate=50/50) to yield didocosyl allylamine (248 mg, 0.368 mmol, yield: 19%).

$^1$H-NMR: δ 3.86 (ddt, 1H, J=17.0 Hz, J=10.1 Hz, J=6.7 Hz), 5.14 Hz (d, 1H, J=17.0 Hz), 5.09 (d, 1H, J=10.1 Hz), 3.07 (d, 2H, J=6.7 Hz), 2.39 (t, 4H, J=7.7 Hz), 1.50-1.06 (m, 80H), 0.88 (t, 6H, J=6.3 Hz).

Synthesis of Didocosylamine

A methylene chloride (3.8 mL) solution of didocosylamine allylamine (516 mg, 0.766 mmol), tetrakispalladium (44.2 mg, 0.0383 mmol) and N,N-dimethylbarbituric acid (359 mg, 2.30 mmol) was stirred at room temperature for 2 hours, then water was added to the reaction mixture, and the mixture was extracted with chloroform twice. The extracts were combined, washed with a saturated aqueous sodium bicarbonate solution and brine, dried with magnesium sulfate, and then concentrated under reduced pressure. Then, the residue was purified with silica gel column chromatography (eluent: hexane/diethyl ether=50/50) to yield didocosylamine (360 mg, 0.567 mmol, yield: 74%).

1H-NMR: 2.59 (t, 4H, J=7.3 Hz), 1.64-1.54 (m, 4H), 1.50-1.44 (m, 4H), 1.32-1.20 (m, 72H).

Synthesis of 4-(Dioctadecylcarbamoyl)benzenesulfonyl Fluoride

Didocosylamine (216 mg, 0.340 mmol) was dissolved in tetrahydrofuran (2.0 mL), triethylamine (0.95 mL, 0.679 mmol) was added to the resulting solution, the solution was cooled to 0° C., and then a solution prepared by dissolving the total amount of the crude purified product of 4-(fluorosulfonyl)benzoyl acid chloride synthesized according to the method shown in Step 1 of Example 1 in dichloromethane (1.4 mL) was added dropwise to the cooled solution and stirred at 0° C. for 1.5 hours. After completion of the reaction, the reaction mixture was added to 1 mol/L hydrochloric acid, and the mixture was extracted with methylene chloride twice. The combined methylene chloride layers were washed with a saturated aqueous sodium hydrogen carbonate solution and brine, and then dried with anhydrous magnesium sulfate and then concentrated under reduced pressure. The residue was purified by silica gel column chromatography (eluent: hexane/diethyl ether=80/20) to yield 4-(dioctadecylcarbamoyl)benzenesulfonic acid fluoride (0.135 g, 0.164 mmol, yield: 48%).

$^1$H-NMR: δ 8.05 (d, 2H, J=8.2 Hz), 7.58 (d, 2H, J=8.2 Hz), 3.49 (t, 2H, J=7.3 Hz), 3.11 (t, 2H, J=7.2 Hz), 1.70-1.60 (m, 4H), 1.54-1.44 (m, 4H), 1.40-1.04 (m, 72H), 0.88 (t, 6H, J=6.8 Hz).

Synthesis of Precursor Compound 8

To a methylene chloride (0.73 mL) solution of 4-(dioctadecylcarbamoyl)benzenesulfonic acid fluoride (112 mg, 0.136 mmol) and 2-dimethyl-5-trimethylsiloxymethyl-5-[(2-nitro-1H-imidazol-1-yl)methyl]-1,3-dioxane (0.146 mmol) synthesized according to Step 7 of Example 1, diazabicycloundecene (44 μL, 0.292 mmol) was added dropwise at 0° C. under stirring. After the reaction mixture was stirred at room temperature for 1 hour, water was added to the reaction mixture, and the mixture was extracted with ethyl acetate twice. The combined extract was washed with brine, dried with magnesium sulfate, and then concentrated under reduced pressure. Then, the residue was purified with silica gel column chromatography (eluent: hexane/ethyl acetate=60/40) to yield the precursor compound 8 (33.4 mg, 0.0321 mmol, yield: 22%).

$^1$H-NMR: δ 7.90 (d, 2H, J=8.2 Hz), 7.54 (d, 2H, J=8.2 Hz), 7.20 (d, 1H, J=1.0 Hz), 7.16 (d, 1H, J=1.0 Hz), 4.74 (s, 2H), 4.01 (s, 2H), 3.72 (d, 2H, J=12.6 Hz), 3.61 (d, 2H, J=12.6 Hz), 3.48 (d, 2H, J=7.8 Hz), 3.14 (d, 2H, J=7.7 Hz), 1.70-1.60 (m, 2H), 1.56-1.06 (m, 78H), 0.88 (t, 6H, J=6.8 Hz).

Comparative Example 1: Synthesis of Conventional Precursor Compound

According to the method described in Example 1 of WO 2013/042668, 2,2-dimethyl-5-[(2-nitro-1H-imidazol-1-yl)methyl]-5-(p-toluenesulfonyloxymethyl)-1,3-dioxane was synthesized.

Example 9: Radioactive Fluorination Using Precursor Compounds 1 to 8

Preparation of 2,2-dimethyl-5-[$^{18}$F]fluoromethyl-5-[(2-nitro-1H-imidazol-1-yl)methyl]-1,3-dioxane To [$^{18}$F]fluoride ion-containing [$^{18}$O]water, an aqueous potassium carbonate solution (42.4 μmol/L, 0.3 mL) and a solution in acetonitrile (0.7 mL) of KRYPTOFIX 222 (trade name, manufactured by Merck KGaA) (14 mg, 37.2 μmol) were added. The resulting solution was heated at 110° C. in a flow of argon gas to evaporate water, and then acetonitrile (0.5 mL×3) was added to the solution and the solution was azeotropically evaporated to dryness. To the dried residue, a solution in acetonitrile (0.3 mL) or acetonitrile/tetrahydrofuran (1/1) mixed solvent (0.4 mL) of the respective precursor compounds 1 to 8 (10 μmol) synthesized according to the methods shown in Examples 1 to 8 were added, and the resulting mixtures were heated at 110° C. for 10 minutes. After completion of the reaction, the mixtures were subjected to TLC analysis under the following conditions, water for injection (10 mL) was added to the mixtures, and the mixtures were allowed to pass through the Sep-Pak (registered trademark) C18 Plas (trade name, manufactured by Nippon Waters K.K.) so that 2,2-dimethyl-5-[$^{18}$F]fluoromethyl-5-[(2-nitro-1H-imidazol-1-yl)methyl]-1,3-dioxane was adsorbed and collected onto the column. The column was washed with water (10 mL), and then a water/acetonitrile=1:1 liquid mixture (2 mL) was allowed to pass through the column to elute 2,2-dimethyl-5-[$^{18}$F]fluoromethyl-5-[(2-nitro-1H-imidazol-1-yl)methyl]-1,3-dioxane.

2,2-Dimethyl-5-[$^{18}$F]fluoromethyl-5-[(2-nitro-1H-imidazol-1-yl)methyl]-1,3-dioxane obtained by the above-described operation was subjected to an HPLC analysis under the following conditions. The identification was performed by verifying that the displacement distance on the TLC plate and the retention time of HPLC were the same as those of the unlabeled sample of 2,2-dimethyl-5-fluoromethyl-5-[(2-nitro-1H-imidazol-1-yl)methyl]-1,3-dioxane synthesized according to the method described in Example 2 of WO 2013/042668.

TLC Conditions
  Plate: TLC glass plate Silica Gel 60F$_{254}$
  Developing solvent: hexane/ethyl acetate=1:3
HPLC Conditions
  Column: YMC-Triart C18 (trade name, size: 4.6 mmφ× 150 mm, manufactured by YMC Co., Ltd.)
  Mobile phase: 50 mM aqueous ammonium carbonate solution/acetonitrile=100/0→30/70 (0→40 min)

Flow rate: 1.0 mL/min
Detector: Ultraviolet-visible absorption spectrophotometer (detection wavelength: 325 nm)

Comparative Example 2: Radioactive Fluorination Using Conventional Precursor Compound Preparation of 2,2-dimethyl-5-[$^{18}$F]fluoromethyl-5-[(2-nitro-1H-imidazol-1-yl)methyl]-1,3-dioxane The preparation of the above-described compound was performed in the same manner as in Example 9 except that, as the precursor compound, 2,2-dimethyl-5-[(2-nitro-1H-imidazol-1-yl)methyl]-5-(p-toluenesulfonyloxymethyl)-1,3-dioxane synthesized according to the method shown in Comparative Example 1 was used.

Evaluation 1: Evaluation of Labeling Reaction for Fluorine-Labeled Compound

Table 2 shows the amounts of radioactivities used in Example 9 and Comparative Example 2, and the amounts of radioactivity and [$^{18}$F]fluorination conversion rate of the obtained products (namely, 2,2-dimethyl-5-[$^{18}$F]fluoromethyl-5-[(2-nitro-1H-imidazol-1-yl)methyl]-1,3-dioxane). The peak area percentage of 2,2-dimethyl-5-[$^{18}$F]fluoromethyl-5-[(2-nitro-1H-imidazol-1-yl)methyl]-1,3-dioxane in the TLC analysis performed after completion of the reaction was taken as the [$^{18}$F]fluorination conversion rate.

As shown in Table 2, the precursor compounds 1 to 8 of the Examples gave approximately the same [$^{18}$F]fluorination conversion rate as that given by the conventional precursor compound.

TABLE 2

| | Amount of radioactivity of [$^{18}$F]fluoride-containing [$^{18}$O] water used (Value corrected at start of synthesis) | Amount of radioactivity of product (measurement timing) | [$^{18}$F] Fluorination conversion rate |
|---|---|---|---|
| Precursor compound 1 | 347 MBq | 144 MBq (44 minutes after start of synthesis) | 61.6% |
| Precursor compound 2 | 620 MBq | 244 MBq (44 minutes after start of synthesis) | 54.1% |
| Precursor compound 3 | 6.3 MBq | 3.6 MBq (35 minutes after start of synthesis) | 73.8% |
| Precursor compound 4 | 315 MBq | 117 MBq (41 minutes after start of synthesis) | 55.9% |
| Precursor compound 5 | 547 MBq | 239 MBq 47 minutes after start of synthesis) | 43.6% |
| Precursor compound 6 | 347 MBq | 105 MBq (60 minutes after start of synthesis) | 32.1% |
| Precursor compound 7 | 401 MBq | 120.1 MBq (39 minutes after start of synthesis) | 49.3% |
| Precursor compound 8 | 472 MBq | 118.5 MBq (48 minutes after start of synthesis) | 45.2% |
| Conventional precursor compound | 477 MBq | 159 MBq (65 minutes after start of synthesis) | 48.2% |

Evaluation 2: Evaluation of Impurities

Table 3 shows the evaluation results based on the HPLC analysis of the amount of the nonradioactive impurities in the samples of 2,2-dimethyl-5-[$^{18}$F]fluoromethyl-5-[(2-nitro-1H-imidazol-1-yl)methyl]-1,3-dioxane obtained in Example 9 and Comparative Example 2. The amount of the remaining precursor compound was quantitatively determined by preparing the calibration curves using a standard sample. The collection percentage was shown in relation to the amount of the precursor compound used in the radioactive fluorination reaction. The amount of impurities having unknown structures was evaluated as converted to the amount of the precursor compound.

Consequently, as shown in Table 3, the precursor compounds 1 to 8 of the Examples were all smaller in the amount of the remaining precursor compound than the conventional compound. Further, the precursor compounds 1, 5, 7 and 8 were smaller in the amount of nonradioactive impurities having unknown structures than the conventional compound.

In Table 3, some of the collection percentages of nonradioactive impurities having unknown structures exceeded 100%; this is probably ascribable to the fact that some UV absorptions were so intense that the amounts of impurities were overestimated.

TABLE 3

| | Amount of remaining precursor compound (Collection percentage) | Amount of nonradioactive impurities* having unknown structures (Collection percentage) |
|---|---|---|
| Precursor compound 1 | Equal to or lower than detection limit value# | 120 μg/mL (5%) |
| Precursor compound 2 | 3 μg/mL (0.1% or less) | 560 μg/mL (21%) |
| Precursor compound 3 | 34 μg/mL (1%) | 1720 μg/mL (64%) |
| Precursor compound 4 | 25 μg/mL (2%) | ca. 5000 μg/mL (180%) * |
| Precursor compound 5 | Equal to or lower than detection limit value# | ca. 300 μg/mL (11%) |
| Precursor compound 6 | 5 μg/mL (0.2%) | ca. 4000 μg/mL (50%) |
| Precursor compound 7 | 6.8 μg/mL (0.5%) | ca. 50 μg/mL (3.7%) |
| Precursor compound 8 | 4.4 μg/mL (0.3%) | ca. 36.6 μg/mL (2.6%) |
| Conventional Precursor compound | 160 μg/mL (6%) | ca. 400 μg/mL (15%) |

Note:
Detection limit value: 1 μg/mL

Evaluation 3: C log Evaluation

The C log values (A) of the precursor compounds 1 to 8 and the conventional precursor compound obtained in Comparative Example 1, and the differences of these values from the C log value (B) of 2,2-dimethyl-5-fluoromethyl-5-[(2-nitro-1H-imidazol-1-yl)methyl]-1,3-dioxane were calculated by using the function of the prediction of physical properties in ChemDraw. Pro. ver 14 for mac. Table 4 shows the results thus obtained.

TABLE 4

|  | A | A-B |
|---|---|---|
| Precursor compound 1 | 11.5 | 10.6 |
| Precursor compound 2 | 7.29 | 6.37 |
| Precursor compound 3 | 3.05 | 2.13 |
| Precursor compound 4 | 4.42 | 3.50 |
| Precursor compound 5 | 7.56 | 6.64 |
| Precursor compound 6 | 6.82 | 5.90 |
| Precursor compound 7 | 17.8 | 16.9 |
| Precursor compound 8 | 21 | 20.1 |
| Conventional precursor compound | 1.8-1.9 | 0.88-0.98 |

Example 10: Synthesis of Low-Oxygen Imaging Agent

By using the precursor compound 1 synthesized by the method shown in Example 1, a low-oxygen imaging agent, namely, 1-(2,2-dihydroxymethyl-3-[$^{18}$F]fluoropropyl)-2-nitroimidazole (the compound 1 of WO2013/042668) was produced.

To [$^{18}$F]fluoride ion-containing [$^{18}$O]water (amount of radioactivity: 306 MBq, the value corrected at the start of synthesis), an aqueous potassium carbonate solution (42.4 µmol/L, 0.3 mL) and a solution in acetonitrile (0.7 mL) solution of KRYPTOFIX 222 (trade name, manufactured by Merck KGaA) (14 mg, 37.2 µmol) were added. The resulting solution was heated at 110° C. in a flow of argon gas to evaporate water, and then acetonitrile (0.5 mL×3) was added to the solution and the solution was azeotropically evaporated to dryness. To the dried residue, a solution in acetonitrile (0.3 mL) of the precursor compound 1 (8 mg, 10 µmol) synthesized in the foregoing Example was added, and the resulting mixture was heated at 110° C. for 10 minutes. After completion of the reaction, water for injection (10 mL) was added to the mixture, the mixture was allowed to pass through the Sep-Pak (registered trademark) C18 Plas (trade name, manufactured by Nippon Waters K.K.), the column was washed with water (10 mL), and then the column was subjected to elution with a water/acetonitrile=1:1 liquid mixture (2 mL). To the eluate, 1 mol/L hydrochloric acid (1.0 mL) was added, and the mixture was heated at 110° C. for 3 minutes. After completion of the reaction, water (10 mL) was added to the mixture, the mixture was allowed to pass through the Sep-Pak (registered trademark) HLB Plas (trade name, manufactured by Nippon Waters K.K.), and 1-(2,2-dihydroxymethyl-3-[$^{18}$F]fluoropropyl)-2-nitroimidazole was adsorbed and collected on the column. The column was washed with water (10 mL), and then ethanol (2 mL) was allowed to pass through the column to elute 1-(2,2-dihydroxymethyl-3-[$^{18}$F]fluoropropyl)-2-nitroimidazole. The obtained amount of radioactivity was 48.5 MBq (87 minutes after the start of the synthesis). The eluted compound was subjected to an HPLC analysis under the following conditions, and consequently the contamination of 26 µg of nonradioactive impurities which were converted to the value equivalent to the precursor compound 1 was verified, and thus it was verified that without performing HPLC purification, a low-oxygen imaging agent having small amounts of nonradioactive impurities was able to be synthesized.

HPLC Conditions

Column: YMC-Triart C18 (trade name, size: 4.6 mmφ× 150 mm, manufactured by YMC Co., Ltd.)

Mobile phase: 50 mM aqueous ammonium carbonate solution/acetonitrile=100/0→30/70 (0→40 min)

Flow rate: 1.0 mL/min

Detector: Ultraviolet-visible absorption spectrophotometer (detection wavelength: 325 nm)

It is apparent that the present invention is not limited to the above embodiment, and may be modified and changed without departing from the scope and spirit of the invention.

The invention claimed is:

1. A labeling precursor compound of a radioactive fluorine-labeled compound represented by the following general formula (1):

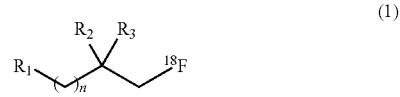

wherein $R_1$ represents an alkynyl group, an alkynyloxy group, an azide group, an azidoalkyl group, an arylazide group, a substituted or unsubstituted monocyclic or condensed polycyclic aryl group, or a substituted or unsubstituted nitrogen-containing heterocycle; $R_2$ and $R_3$ each independently represent an alkyl group having 1 to 6 carbon atoms, or a hydroxyalkyl group having 1 to 6 carbon atoms, wherein the hydroxy group may be protected with a protecting group; and n is an integer of 1 or 2, which is represented by the following general formula (2):

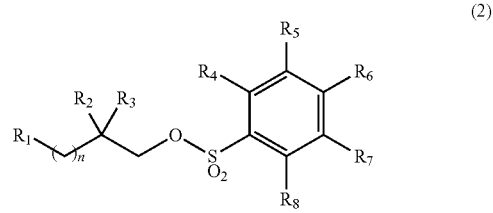

wherein $R_1$, $R_2$, $R_3$ and n are the same as those in the above-described general formula (1); $R_6$ represents a straight-chain alkyl group having 8 to 16 carbon atoms, or —$CONR_{11}R_{12}$ wherein $R_{11}$ and $R_{12}$ each independently represent an alkyl group having 4 to 24 carbon atoms, or a substituted or unsubstituted monocyclic or condensed polycyclic aryl group; and $R_4$, $R_5$, $R_7$ and $R_8$ each independently represent a hydrogen atom, an alkyl group having 1 to 4 carbon atoms, or an alkoxy group having 1 to 4 carbon atoms.

2. The labeling precursor compound according to claim 1, wherein the difference between the C log P of the radioactive fluorine-labeled compound represented by the above-described general formula (1) and the C log P of the precursor compound represented by the above-described general formula (2) is 1 or more.

3. The labeling precursor compound according to claim 1, wherein in the above-described general formula (2), $R_6$ represents a straight-chain alkyl group having 8 to 16 carbon atoms or —CONR$_{11}$R$_{12}$ wherein R$_{11}$ and R$_{12}$ each independently represent a straight-chain alkyl group having 4 to 24 carbon atoms or a substituted or unsubstituted condensed polycyclic aryl group, and R$_4$, R$_5$, R$_7$ and R$_8$ each represent a hydrogen atom.

4. The labeling precursor compound according to claim 1, wherein in the above-described general formulas (1) and (2), R$_1$ represents a substituted or unsubstituted nitrogen-containing heterocycle.

5. The labeling precursor compound according to claim 4, wherein R$_1$ is a group represented by the following formula (3):

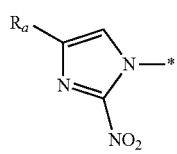

wherein R$_a$ is a hydrogen atom, a methyl group or a hydroxymethyl group.

6. A method for producing a radioactive fluorine-labeled compound, which comprises a step of allowing the labeling precursor compound represented by the general formula (2) according to claim 1 to react with [$^{18}$F]fluoride ion, whereby a radioactive fluorine-labeled compound is obtained which is represented by the following general formula (1):

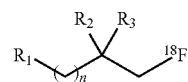

wherein R$_1$ represents an alkynyl group, an alkynyloxy group, an azide group, an azidoalkyl group, an arylazide group, a substituted or unsubstituted monocyclic or condensed polycyclic aryl group or a substituted or unsubstituted nitrogen-containing heterocycle, R$_2$ and R$_3$ each independently represent an alkyl group having 1 to 6 carbon atoms, or a hydroxyalkyl group having 1 to 6 carbon atoms, wherein the hydroxy group may be protected with a protecting group, and n is an integer of 1 or 2.

7. The method according to claim 6, which further comprises a step of adding a reaction mixture containing the radioactive fluorine-labeled compound of the above-described general formula (1) resulting from the reaction of the labeling precursor compound with [$^{18}$F]fluoride to a reverse phase cartridge column, and a step of eluting the radioactive fluorine-labeled compound of the above-described general formula (1) from the reverse phase cartridge column.

* * * * *